United States Patent
Banowski et al.

(10) Patent No.: US 9,724,286 B2
(45) Date of Patent: Aug. 8, 2017

(54) ANTIPERSPIRANT COSMETIC AGENTS HAVING POLYPHOSPHORIC ACIDS

(71) Applicant: Henkel AG & Co. KGaA, Duesseldorf (DE)

(72) Inventors: Bernhard Banowski, Duesseldorf (DE); Marcus Claas, Hilden (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/080,842

(22) Filed: Mar. 25, 2016

(65) Prior Publication Data

US 2016/0206541 A1  Jul. 21, 2016

Related U.S. Application Data

(63) Continuation of application No. PCT/DE2014/200514, filed on Sep. 26, 2014.

(30) Foreign Application Priority Data

Oct. 15, 2013  (DE) .................. 10 2013 220 770

(51) Int. Cl.
 *A61K 8/28* (2006.01)
 *A61K 8/55* (2006.01)
 *A61K 8/26* (2006.01)
 *A61Q 15/00* (2006.01)
 *A61K 8/891* (2006.01)
 *A61K 8/92* (2006.01)

(52) U.S. Cl.
 CPC .............. *A61K 8/55* (2013.01); *A61K 8/26* (2013.01); *A61K 8/28* (2013.01); *A61K 8/891* (2013.01); *A61K 8/922* (2013.01); *A61Q 15/00* (2013.01); *A61K 2800/596* (2013.01)

(58) Field of Classification Search
 CPC ... A61K 8/55; A61K 8/26; A61K 8/28; A61K 8/891; A61K 8/922; A61Q 11/00
 See application file for complete search history.

(56) References Cited

U.S. PATENT DOCUMENTS

| | | |
|---|---|---|
| 2,571,030 A | 10/1951 | Govett et al. |
| 3,542,919 A | 11/1970 | Buth et al. |
| 3,553,316 A | 1/1971 | Rubino |
| 3,887,692 A | 6/1975 | Gilman |
| 3,904,741 A | 9/1975 | Jones et al. |
| 3,991,176 A | 11/1976 | Rubino |
| 4,017,599 A | 4/1977 | Rubino |
| 4,359,456 A | 11/1982 | Gosling et al. |
| 4,775,528 A | 10/1988 | Callaghan et al. |
| 5,643,558 A | 7/1997 | Provancal et al. |
| 5,972,321 A | 10/1999 | Kligerman et al. |
| 6,010,688 A | 1/2000 | Shen |
| 6,042,816 A | 3/2000 | Shen |
| 6,074,632 A | 6/2000 | Shen |
| 6,245,325 B1 | 6/2001 | Shen |
| 6,436,381 B1 | 8/2002 | Carrillo et al. |
| 6,649,152 B2 | 11/2003 | Carrillo et al. |
| 6,663,854 B1 | 12/2003 | Shen et al. |
| 6,923,952 B2 | 8/2005 | Allen et al. |
| 7,105,691 B2 | 9/2006 | Holerca et al. |
| 2003/0232026 A1 | 12/2003 | Kajino et al. |
| 2004/0009133 A1 | 1/2004 | Kolodzik et al. |
| 2008/0069788 A1 | 3/2008 | Roesch |

FOREIGN PATENT DOCUMENTS

| | | | |
|---|---|---|---|
| DE | 102006004957 A1 | 8/2007 | |
| DE | 102007028508 | * 4/2008 | ............... A61K 8/44 |
| DE | 102007028508 A1 | 4/2008 | |
| EP | 0183171 A2 | 6/1986 | |
| EP | 0191628 A2 | 8/1986 | |
| EP | 0308937 A2 | 3/1989 | |
| GB | 1347950 | 2/1974 | |
| GB | 2048229 A | 12/1980 | |

OTHER PUBLICATIONS

PCT International Search Report (PCT/DE2014/200514) dated Jan. 28, 2015.

* cited by examiner

*Primary Examiner* — Nannette Holloman
(74) *Attorney, Agent, or Firm* — P. Scott Smith

(57) ABSTRACT

The invention relates to an antiperspirant cosmetic agent, including a) at least one substance, selected form the group of cosmetic oils that are liquid at 20° C. and 1.013 hPa, aromatic substances, and waxes, b) at least one antiperspirant aluminum salt in a total amount of 0.1 to 80 wt %, with respect to the total weight of the antiperspirant cosmetic agent, and c) at least one compound of formula (PP-I)

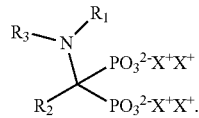

(PP-I)

18 Claims, No Drawings

ANTIPERSPIRANT COSMETIC AGENTS HAVING POLYPHOSPHORIC ACIDS

FIELD OF THE INVENTION

The present invention generally relates to an antiperspirant cosmetic agent including at least one antiperspirant aluminum salt and at least one polyphosphoric acid, wherein the addition of the at least one polyphosphoric acid results in an enhancement of the blocking of the sweat gland(s) and/or in a blocking of the sweat gland(s).

The present invention further relates to the use of a combination of at least one antiperspirant aluminum salt and at least one polyphosphoric acid for reducing and/or preventing axillary perspiration.

Moreover, the present invention relates to a non-therapeutic cosmetic method for preventing and/or reducing perspiration of the body, in which the antiperspirant agent according to the invention is applied to the skin, and more particularly to the skin of the axilla region.

Finally, the present invention relates to the use of a polyphosphoric acid for enhancing the blocking of the sweat gland(s) and/or for blocking the sweat gland(s).

BACKGROUND OF THE INVENTION

Washing, cleaning, and caring for one's body is a basic human need, and modern industry is continually attempting to satisfy these needs of humans in a variety of ways. The lasting elimination, or at least reduction, of body odor and underarm perspiration is particularly important for daily hygiene. Numerous special deodorizing or antiperspirant body care agents are known in the related art, which were developed for use in body regions that have a high density of sweat glands, in particular in the axilla region. These are formulated in a wide variety of forms of administration, for example as powders, in stick form, as aerosol sprays, pump sprays, liquid and gel-like roll-on applications, creams, gels, and as saturated flexible substrates (deodorant wipes).

In addition to at least one oil or a fat substance and an odorous substance component or a perfume, cosmetic antiperspirants of the related art include at least one antiperspirant salt.

The antiperspirant salts used in antiperspirants decrease the secretion of sweat by the body by temporarily constricting or clogging the excretory ducts of the sweat glands, whereby the amount of sweat can be reduced by approximately 20 to 60 percent. Furthermore, they have an additionally deodorizing effect due to the antimicrobial action thereof.

The antiperspirant salt that is customarily used is activated basic aluminum and aluminum-zirconium halides, as they are described in documents EP 0308937 A2, EP 0183171 A2, U.S. Pat. No. 4,359,456 A, and EP 0191628. In addition, aluminum and aluminum-zirconium halides that are stabilized with organic acids as complexing ligands can be used, as they are disclosed in documents U.S. Pat. No. 3,542,919 A, U.S. Pat. No. 3,553,316 A, U.S. Pat. No. 3,991,176 A, and WO 2005/092795 A1, for example.

One disadvantage of the above-mentioned activated basic aluminum and aluminum-zirconium halides of the related art is that the polymer structure changes in an aqueous solution with an extended storage time and/or with the use of protic solvents, or that the action of non-activated, cost-effective aluminum salts is limited, whereby a significant reduction in the secretion of sweat by the body through a temporary constriction and/or clogging of the excretory ducts of the sweat glands cannot always be ensured.

A need therefore exists for antiperspirant cosmetic agents that exhibit no significant decrease in the antiperspirant action even during long storage periods and/or with the use of high amounts of protic solvents. Moreover, the antiperspirants should be cost-effective to produce.

It was the object of the present invention to provide an antiperspirant cosmetic agent that prevents, or at least lessens, the drawbacks from the related art and is able to ensure reliable clogging of the excretory ducts of the sweat glands even during extended storage periods and/or in the presence of protic solvents.

Surprisingly, it has now been found that the use of polyphosphoric acids in cosmetic agents that include antiperspirant aluminum salts results in significantly increased hydrogel formation of these agents at pH values that prevail exclusively within the excretory ducts of the sweat glands, thereby ensuring effective clogging of these excretory ducts. Due to the pH selectivity, hydrogel formation takes place neither in the antiperspirant cosmetic composition nor on the skin outside, so that the addition of the polyphosphoric acid does not cause a decreased efficacy of the antiperspirant cosmetic agent as a result of premature hydrogel formation.

Furthermore, other desirable features and characteristics of the present invention will become apparent from the subsequent detailed description of the invention and the appended claims, taken in conjunction with this background of the invention.

BRIEF SUMMARY OF THE INVENTION

An antiperspirant cosmetic agent, comprising: at least one substance selected from the group consisting of cosmetic oils that are liquid at 20° C. and 1,013 hPa, odorous substances and waxes; at least one antiperspirant aluminum salt in a total amount of 0.1 to 80 wt. %, based on the total weight of the antiperspirant cosmetic agent; and at least one compound of formula (PP-I)

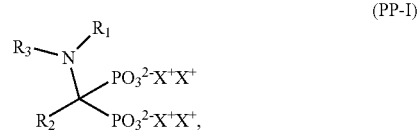

(PP-I)

where $R^1$ denotes hydrogen or a linear or branched alkyl group having 1 to 6 carbon atoms; $R^2$ and $R^3$, each independently of one another, denote a linear or branched alkyl group having 1 to 6 carbon atoms, or $R^2$ and $R^3$ form a cyclic group having 4 to 8 carbon atoms and optionally one heteroatom, selected from the group consisting of N, O, and S; and $X^+$ denotes $H^+$, $Li^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt.

Use of a combination of at least one substance, selected from the group consisting of cosmetic oils that are liquid at 20° C. and 1,013 hPa, odorous substances and waxes, at least one antiperspirant aluminum salt in a total amount of 0.1 to 80 wt. %, based on the total weight of the combination, and at least one compound of formula (PP-I),

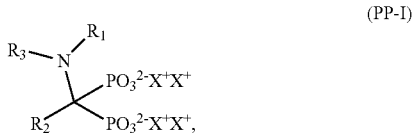

(PP-I)

where $R^1$ denotes hydrogen or a linear or branched alkyl group having 1 to 6 carbon atoms; $R^2$ and $R^3$, each independently of one another, denote a linear or branched alkyl group having 1 to 6 carbon atoms, or $R^2$ and $R^3$ form a cyclic group having 4 to 8 carbon atoms and optionally one heteroatom, selected from the group consisting of N, O, and S; and $X^+$ denotes $H^+$, $Li^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt for reducing and/or preventing perspiration.

A non-therapeutic cosmetic method for preventing and/or reducing perspiration of the body, in which an antiperspirant cosmetic agent, including at least one substance selected from the group consisting of cosmetic oils that are liquid at 20° C. and 1,013 hPa, odorous substances and waxes, at least one antiperspirant aluminum salt in a total amount of 0.1 to 80 wt. %, based on the total weight of the antiperspirant cosmetic agent, and at least one compound of formula (PP-I), is applied to the skin, and more particularly to the skin of the axilla region.

Use of the at least one compound of formula (PP-I)

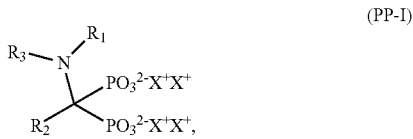

(PP-I)

where $R^1$ denotes hydrogen or a linear or branched alkyl group having 1 to 6 carbon atoms; $R^2$ and $R^3$, each independently of one another, denote a linear or branched alkyl group having 1 to 6 carbon atoms, or $R^2$ and $R^3$ form a cyclic group having 4 to 8 carbon atoms and optionally one heteroatom, selected from the group consisting of N, O, and S; and $X^+$ denotes $H^+$, $Li^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt for enhancing the blocking of the sweat gland(s) and/or for blocking the sweat gland(s).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention relates to an antiperspirant cosmetic agent, including
a) at least one substance selected from the group consisting of cosmetic oils that are liquid at 20° C. and 1,013 hPa, odorous substances and waxes;
b) at least one antiperspirant aluminum salt in a total amount of 0.1 to 80 wt. %, based on the total weight of the antiperspirant cosmetic agent; and
c) at least one compound of formula (PP-I)

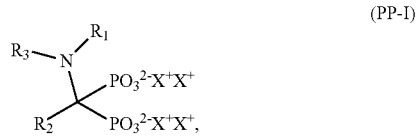

(PP-I)

where
$R^1$ denotes hydrogen or a linear or branched alkyl group having 1 to 6 carbon atoms,
$R^2$ and $R^3$, each independently of one another, denote a linear or branched alkyl group having 1 to 6 carbon atoms, or $R^2$ and $R^3$ form a cyclic group having 4 to 8 carbon atoms and optionally one heteroatom, selected from the group consisting of N, O, and S, and
$X^+$ denotes $H^+$, $Li^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt.

Without being limited to this theory, combining antiperspirant aluminum salts with special compounds of formula (PP-I) results in a hydrogel formation of the antiperspirant aluminum salt and of the compound of formula (PP-I) solely at extremely specific pH values. Due to the extremely selective formation of the hydrogel at pH values that are solely present within the excretory ducts of the sweat glands, effective clogging of the excretory ducts of the sweat glands is ensured, without the antiperspirant action of the cosmetic agent according to the invention being decreased by a premature undesirable hydrogel formation as a result of the addition of the compound of formula (PP-I). In this way, an outstanding antiperspirant action can be ensured, even after extended storage periods and/or with the presence of high amounts of protic solvents.

According to the invention, the term "antiperspirant" shall be understood to mean the decrease or reduction of the perspiration of the body's sweat glands.

Moreover, the term "cosmetic oil" within the meaning of the present invention shall be understood to mean an oil that is suitable for cosmetic use and not miscible with water. The cosmetic oil used according to the invention furthermore involves neither odorous substances nor essential oils.

Additionally, the term "odorous substances" within the meaning of the present invention shall be understood to mean substances having a molar mass of 74 to 300 g/mol, which include at least one osmophoric group in the molecule and have an odor and/or a flavor, which is to say they are capable of stimulating the receptors of the hair cells of the olfactory system. Osmophoric groups are groups that are covalently bound to the molecular skeleton in the form of hydroxy groups, formyl groups, oxo groups, alkoxy carbonyl groups, nitrile groups, nitro groups, azide groups and the like. In this connection, the term "odorous substances" within the meaning of the present invention also covers perfume oils, perfumes, or perfume oil components that are liquid at 20° C. and 1,013 hPa.

Moreover, the term "waxes" within the scope of the present invention shall be understood to mean substances that are kneadable or solid to brittle-hard at 20° C., have a coarse to microcrystalline structure, and are translucent to colors to opaque, but not vitreous. These substances furthermore melt above 25° C. without decomposing, are easily liquid (low viscosity) just above the melting point, have a highly temperature-dependent consistency and solubility, and can be polished under light pressure.

The term "volatile cosmetic oil" according to the invention refers to cosmetic oils that, at 20° C. and an ambient pressure of 1,013 hPa, have a vapor pressure of 2.66 Pa to 40,000 Pa (0.02 to 300 mm Hg), especially of 10 to 12,000 Pa (0.1 to 90 mm Hg), more preferably of 13 to 3,000 Pa (0.1 to 23 mm Hg), and in particular of 15 to 500 Pa (0.1 to 4 mm Hg).

Moreover, the term "non-volatile cosmetic oils" within the meaning of the present invention shall be understood to mean cosmetic oils that, at 20° C. and an ambient pressure of 1,013 hPa, have a vapor pressure of less than 2.66 Pa (0.02 mm Hg).

Furthermore, the term "fatty acid," as it is used within the scope of the present invention, shall be understood to mean aliphatic carboxylic acids that include unbranched or branched carbon groups having 4 to 40 carbon atoms. The fatty acids used within the scope of the present invention can be both naturally occurring and synthetically produced fatty acids. The fatty acids can moreover be monounsaturated or polyunsaturated.

Finally, the term "fatty alcohol" within the scope of the present invention shall be understood to mean aliphatic, monohydric, primary alcohols that include unbranched or branched hydrocarbon groups having 4 to 40 carbon atoms. The fatty alcohols used within the scope of the invention can also be monounsaturated or polyunsaturated.

Unless indicated otherwise, in the present invention the wt. % information refers to the total weight of the antiperspirant cosmetic agents according to the invention, without optionally present propellants.

According to a preferred embodiment of the present invention, the cosmetic oil that is liquid at 20° C. and 1,013 hPa is selected from the group consisting of (i) volatile cyclic silicone oils, in particular cyclotrisiloxane, cyclotetrasiloxane, cyclopentasiloxane, and cyclohexasiloxane, and linear silicone oils having 2 to 10 siloxane units, in particular hexamethyldisiloxane, octamethyltrisiloxane, decamethyltetrasiloxane;

(ii) volatile non-silicone oils, in particular liquid paraffin oils and isoparaffin oils, such as isodecane, isoundecane, isododecane, isotridecane, isotetradecane, isopentadecane, isohexadecane, and isoeicosane;

(iii) non-volatile silicone oils, in particular higher molecular weight linear polyalkylsiloxanes;

(iv) non-volatile non-silicone oils, in particular the esters of linear or branched saturated or unsaturated $C_{2-30}$ fatty alcohols having linear or branched saturated or unsaturated $C_{2-30}$ fatty acids, which may be hydroxylated, the $C_8$ to $C_{22}$ fatty alcohol esters of monovalent or polyvalent $C_2$ to $C_7$ hydroxycarboxylic acids, the triethyl citrates, the branched saturated or unsaturated $C_{6-30}$ fatty alcohols, the mono-, di- and triglycerides of linear or branched, saturated or unsaturated, optionally hydroxylated $C_{8-30}$ fatty acids, the dicarboxylic acid esters of linear or branched $C_2$ to $C_{10}$ alkanols, the addition products of ethylene oxide and/or propylene oxide to monohydric or polyhydric $C_{3-22}$ alkanols, which may optionally be esterified, the symmetrical, asymmetrical or cyclic esters of carbonic acid with fatty alcohols, the esters of dimers of unsaturated $C_{12-22}$ fatty acids with monohydric, linear, branched and cyclic $C_{2-18}$ alkanols or $C_{2-6}$ alkanols, the benzoic acid esters of linear or branched $C_{8-22}$ alkanols, such as benzoic acid-$C_{12-15}$-alkyl esters and benzoic acid isostearyl esters and benzoic acid octyldodecyl esters, the synthetic hydrocarbons, such as polyisobutene and polydecene, the alicyclic hydrocarbons; and (v) the mixtures thereof.

The use of volatile silicone oils and volatile non-silicone oils in the antiperspirant cosmetic agents according to the invention results in a dryer skin sensation and a more rapid release of the antiperspirant aluminum salt.

The cyclic volatile silicone oils usable within the scope of the invention have a vapor pressure of 13 to 15 Pa (0.1 mm Hg) at 20° C. and an ambient pressure of 1,013 hPa. Moreover, it is also possible according to the invention to use a low molecular weight phenyl trimethicone having a vapor pressure of approximately 2,000 Pa (15 mm Hg) at 20° C. and an ambient pressure of 1,013 hPa as the linear volatile silicone oil. Due to the high persistence of cyclodimethicones in the environment, however, it may be preferred according to the invention if 0 to less than 1 wt. %, especially 0 to less than 0.1 wt. %, cyclic volatile silicone oils is used in the antiperspirant cosmetic agents according to the invention.

According to the invention, preferably volatile non-silicone oils in the form of $C_{10-13}$ isoparaffin mixtures having a vapor pressure of 10 to 400 Pa (0.08 to 3 mm Hg), especially of 13 to 100 Pa (0.1 to 0.8 mm Hg), at 20° C. and an ambient pressure of 1,013 hPa are used. It is preferred within the scope of the present invention if the volatile $C_8$ to $C_{16}$ isoparaffin is present in a total amount of 1 to 60 wt. %, especially of 3 to 45 wt. %, preferably of 5 to 40 wt. %, and in particular of 8 to 20 wt. %, based on the total weight of the antiperspirant cosmetic agent. Of course it is likewise possible to formulate antiperspirant cosmetic agents according to the invention with a low content of volatile oils, which is to say with 0.5 to 15 wt. % of volatile oils, or even without volatile oils, based on the total weight of the antiperspirant cosmetic agent.

So as to mask insoluble components, such as talcum or antiperspirant aluminum salts dried on the skin, it may be preferred according to the invention if the antiperspirant cosmetic agents include a non-volatile silicone oil and/or a non-volatile non-silicone oil.

In this connection, preferred antiperspirant cosmetic agents according to the invention include at least one ester of the linear or branched saturated or unsaturated fatty alcohols including 2 to 30 carbon atoms with linear or branched saturated or unsaturated fatty acids including 2 to 30 carbon atoms, which may be hydroxylated, in a total amount of 1 to 30 wt. %, especially of 5 to 26 wt. %, preferably of 9 to 24 wt. %, and in particular of 12 to 17 wt. %, based on the total weight of the antiperspirant cosmetic agent.

Within the scope of the present invention, linear polyalkylsiloxanes having a kinematic viscosity at 25° C. of 5 to 2,000 cSt, in particular linear polydimethylsiloxanes having a kinematic viscosity at 25° C. of 5 to 2,000 cSt, especially of 10 to 350 cSt, and in particular of 50 to 100 cSt, can be used as non-volatile silicone oils. The above-mentioned non-volatile silicone oils are available under the trade name Dow Corning® 200 and Xiameter PMX from Dow Corning and Xiameter, respectively. Further preferred non-volatile silicone oils are phenyl trimethicones having a kinematic viscosity at 25° C. of 10 to 100 cSt, especially of 15 to 30 cSt, and cetyl dimethicones.

Further preferred according to the invention is the use of mixtures of the above-mentioned cosmetic oils, in particular of non-volatile and volatile cosmetic oils, since in this way parameters such as skin sensation, visibility of the residue, and stability of the antiperspirant cosmetic agent according to the invention can be set, and the agent can thus be better adapted to the needs of the consumers.

It is preferred within the scope of the present invention if the cosmetic oil that is liquid at 20° C. and 1,013 hPa is present in a total amount of 1 to 95 wt. %, especially of 10 to 85 wt. %, preferably of 20 to 70 wt. %, more preferably of 35 to 70 wt. %, and in particular of 50 to 60 wt. %, based on the total weight of the antiperspirant cosmetic agent.

However, it may also be preferred if the cosmetic oil that is liquid at 20° C. and 1,013 hPa is present in a total amount of 0.2 to 70 wt. %, especially of 2 to 60 wt. %, preferably of 3 to 50 wt. %, more preferably of 5 to 35 wt. %, and in particular of 8 to 20 wt. %, based on the total weight of the antiperspirant cosmetic agent. In this connection, it may also be provided according to the invention that the antiperspirant agents according to the invention include less than 0.2 wt. %, especially less than 0.1 wt. %, and in particular 0 wt. % of the cosmetic oil that is liquid at 20° C. and 1,013 hPa. The use of only extremely small amounts of the cosmetic oil that is liquid at 20° C. and 1,013 hPa is preferred in particular in antiperspirant cosmetic agents according to the invention that are present in aqueous, aqueous-alcoholic or aqueous-glycolic form.

According to a preferred embodiment of the present invention, the odorous substance is selected from the group consisting of
(i) esters, in particular benzyl acetate, phenoxyethyl isobutyrate, p-tert-butylcyclohexyl acetate, linalyl acetate, dimethyl benzyl carbinyl acetate (DMBCA), phenylethyl acetate, benzyl acetate, ethyl methylphenyl glycinate, allyl cyclohexyl propionate, styrallyl propionate, benzyl salicylate, cyclohexyl salicylate, floramate, melusate, and jasmecyclate;
(ii) ethers, in particular benzyl ethyl ethers and Ambroxan;
(iii) aldehydes, in particular linear alkanals having 8 to 18 carbon atoms, citral, citronellal, citronellyl oxy acetaldehyde, cyclamen aldehyde, lilial and bourgeonal;
(iv) ketones, in particular jonone, alpha-isomethyl ionone and methyl cedryl ketone;
(v) alcohols, in particular anethol, citronellol, eugenol, geraniol, linalool, phenylethyl alcohol and terpineol;
(vi) hydrocarbons, in particular terpenes such as limonene and pinene; and
(vii) the mixtures thereof.

Preferably, however, mixtures of different odorous substances are used, which together produce an appealing odorous note.

Antiperspirant cosmetic agents according to the invention that have a particularly appealing odor are obtained when the odorous substance is present in a total amount of 0.00001 to 10 wt. %, especially 0.001 to 9 wt. %, preferably 0.01 to 8 wt. %, more preferably 0.5 to 7 wt. %, and in particular 1 to 6 wt. %, based on the total weight of the antiperspirant cosmetic agent. In this connection, however, it may also be provided that the odorous substance is present in a total amount of 0.00001 to 5 wt. %, especially 0.001 to 4 wt. %, preferably 0.01 to 3 wt. %, more preferably 0.1 to 2 wt. %, and in particular 0.2 to 1.5 wt. %, based on the total weight of the propellant-containing antiperspirant cosmetic agent.

According to a further preferred embodiment of the present invention, the wax is selected from the group consisting of
(i) fatty acid glycerol mono-, di-, and triesters;
(ii) Butyrospermum Parkii (shea butter);
(iii) esters of saturated, monohydric $C_{8-18}$ alcohols with saturated $C_{12-18}$ monocarboxylic acids;
(iv) linear primary $C_{12}$ to $C_{24}$ alkanols;
(v) esters of a saturated, monohydric $C_{16}$ to $C_{60}$ alkanol and a saturated $C_8$ to $C_{36}$ monocarboxylic acid, in particular cetyl behenate, stearyl behenate, and $C_{20}$ to $C_{40}$ alkyl stearate;
(vi) glycerol triesters of saturated linear $C_{12}$ to $C_{30}$ carboxylic acids, which may be hydroxylated, in particular hydrogenated palm oil, hydrogenated coconut oil, hydrogenated castor oil, glyceryl tribehenate, and glyceryltri-12-hydroxy stearate;
(vii) natural plant-based waxes, in particular candelilla wax, carnauba wax, Japan wax, sugar cane wax, ouricury wax, cork wax, sunflower wax, fruit waxes;
(viii) animal waxes, in particular beeswax, shellac wax, and cetaceum;
(ix) synthetic waxes, in particular montan ester waxes, hydrogenated jojoba waxes and sasol waxes, polyalkylene waxes and polyethylene glycol waxes, $C_{20}$ to $C_{40}$ dialkyl esters of dimer acids, $C_{30-50}$ alkyl beeswax, and alkyl and alkyl aryl esters of dimeric fatty acids, paraffin waxes; and
(x) the mixtures thereof.

Commercial products bearing the INCI name Cocoglycerides, in particular the commercial products Novata® (from BASF), particularly preferably Novata® AB, a mixture of $C_{12-18}$ mono-, di-, and triglycerides that melts in the range from 30 to 32° C., and the products of the Softisan series (Sasol Germany GmbH) bearing the INCI name Hydrogenated Cocoglycerides, in particular Softisan 100, 133, 134, 138, 142, are particularly preferred. Further preferred esters of saturated, monohydric $C_{12-18}$ alcohols with saturated $C_{12-18}$ monocarboxylic acids are stearyl laurate, cetearyl stearate (such as Crodamol® CSS), cetyl palmitate (such as Cutina® CP), and myristyl myristate (such as Cetiol® MM). Furthermore a $C_{20}$ to $C_{40}$ alkyl stearate is preferably used as the wax component. This ester is known under the name Kester Wax® K82H or Kester Wax® K80H and is sold by Koster Keunen Inc.

It is preferred within the scope of the present invention if the wax is present in a total amount of 0.01 to 20 wt. %, especially 3 to 20 wt. %, preferably 5 to 18 wt. %, and in particular 6 to 15 wt. %, based on the total weight of the antiperspirant cosmetic agent.

A particularly good antiperspirant action within the scope of the present invention is achieved when the antiperspirant aluminum salt is present in a total amount of 1 to 40 wt. %, especially of 3 to 35 wt. %, preferably of 4 to 32 wt. %, more preferably of 5 to 28 wt. %, still more preferably of 8 to 25 wt. %, and in particular of 12 to 22 wt. %, based on the total weight of the antiperspirant cosmetic agent. However, it may also be provided that the antiperspirant aluminum salt is present in a total amount of 0.1 to 20 wt. %, especially of 0.5 to 15 wt. %, preferably of 1 to 12 wt. %, more preferably of 1.5 to 10 wt. %, and in particular of 2 to 8 wt. %, based on the total weight of the propellant-containing antiperspirant composition.

Within the scope of the present invention, the antiperspirant aluminum salt may be selected from the group consisting of
(i) water-soluble astringent inorganic salts of aluminum, in particular aluminum chlorohydrate, aluminum sesquichlorohydrate, aluminum dichlorohydrate, aluminum hydroxide, potassium aluminum sulfate, aluminum bromohydrate, aluminum chloride, aluminum sulfate;
(ii) water-soluble astringent organic salts of aluminum, in particular aluminum chlorohydrex propylene glycol, aluminum chlorohydrex polyethylene glycol, aluminum propylene glycol complexes, aluminum sesquichlorohydrex propylene glycol, aluminum sesquichlorohydrex polyethylene glycol, aluminum propylene glycol dichlorohydrex, aluminum polyethylene glycol dichlorohydrex, aluminum undecylenoyl collagen amino acid, sodium aluminum lactate, sodium aluminum chlorohydroxy lactate, aluminum lipoamino acids, aluminum lactate, aluminum chlorohydroxy allantoinate, sodium aluminum chlorohydroxy lactate;

(iii) water-soluble astringent inorganic aluminum-zirconium salts, in particular aluminum-zirconium trichlorohydrate, aluminum-zirconium tetrachlorohydrate, aluminum-zirconium pentachlorohydrate, aluminum-zirconium octachlorohydrate;

(iv) water-soluble astringent organic aluminum-zirconium salts, in particular aluminum-zirconium propylene glycol complexes, aluminum-zirconium trichlorohydrex glycine, aluminum-zirconium tetrachlorohydrex glycine, aluminum-zirconium pentachlorohydrex glycine, aluminum-zirconium octachlorohydrex glycine; and (v) the mixtures thereof.

According to the invention, the term "antiperspirant aluminum salts" shall be understood not to include any aluminosilicates and zeolites. Moreover, according to the invention "water-soluble aluminum salts" shall be understood to mean those salts which have a solubility of at least 3 wt. % at 20° C., which is to say at least 3 g of the antiperspirant aluminum salt dissolves in 97 g of water at 20° C.

Particularly preferred inorganic aluminum salts are selected from aluminum chlorohydrate, in particular aluminum chlorohydrate of the general formula $[Al_2(OH)_5Cl.1-6H_2O]_n$, preferably $[Al_2(OH)_5Cl.2-3H_2O]_n$, which may be present in non-activated (polymerized) or in activated (depolymerized) form, and aluminum chlorohydrate of the general formula $[Al_2(OH)_4Cl_2.1-6H_2O]_n$, preferably $[Al_2(OH)_4Cl_2.2-3H_2O]_n$, which may be present in non-activated (polymerized) or in activated (depolymerized) form. The production of such antiperspirant aluminum salts is disclosed in documents U.S. Pat. No. 3,887,692 A, U.S. Pat. No. 3,904,741 A, U.S. Pat. No. 4,359,456 A, GB 2048229 A, and GB 1347950 A, for example.

Particularly preferred antiperspirant aluminum salts according to the invention are selected from what are known as "activated" aluminum salts, which are also referred to as enhanced-activity active antiperspirant ingredients. Such active ingredients are known from the prior art and are also commercially available. Production of the same is disclosed in documents GB 2048229 A, U.S. Pat. No. 4,775,528 A, and U.S. Pat. No. 6,010,688 A. Activated aluminum salts are generally produced by heat treating a dilute solution of the corresponding salt (such as a solution containing 10 wt. % salt), so as to increase the HPLC peak 4 to peak 3 area ratio of the same. The activated salt can subsequently be dried to obtain a powder, in particular spray-dried. In addition to spray drying, drum drying also suited, for example. Activated aluminum salts typically have an HPLC peak 4 to peak 3 area ratio of at least 0.4, especially of at least 0.7, and in particular of at least 0.9, wherein at least 70% of the aluminum can be assigned to these HPLC peaks.

In this connection, "activated" aluminum-zirconium salts are likewise known, which have a high HPLC peak 5 aluminum content, in particular a peak 5 area of at least 33%, especially of at least 45%, based on the total surface area under peaks 2-5, as measured by way of HPLC, of a 10% by weight aqueous solution of the active ingredient under conditions in which the aluminum species are dissolved in at least four successive peaks (referred to as peaks 2-5). Preferred aluminum-zirconium salts having a high HPLC peak 5 aluminum content (also referred to as "E$^5$AZCH") are disclosed in documents U.S. Pat. No. 6,436,381 A and U.S. Pat. No. 6,649,152 A, for example. Furthermore, the above-mentioned activated aluminum-zirconium salts can additionally be stabilized with a water-soluble strontium salt and/or a water-soluble calcium salt, as they are disclosed in document U.S. Pat. No. 6,923,952 A, for example.

It is likewise possible according to the invention to use antiperspirant aluminum salts as non-aqueous solutions or solubilizates of an activated antiperspirant aluminum or aluminum-zirconium salt, for example in accordance with document U.S. Pat. No. 6,010,688 A. As a result of the addition of an effective amount of a polyhydric alcohol comprising 3 to 6 carbon atoms and 3 to 6 hydroxyl groups, preferably propylene glycol, sorbitol and pentaerythritol, such aluminum or aluminum-zirconium salts are stabilized against the loss of the activation of the salt.

Particularly preferred are also complexes of activated antiperspirant aluminum or aluminum-zirconium salts with a polyhydric alcohol, which include 20 to 50 wt. %, especially 20 to 42 wt. %, activated antiperspirant aluminum or aluminum-zirconium salt and 2 to 16 wt. % molecularly bound water, wherein the remainder to make up 100 wt. % is at least one polyhydric alcohol comprising 3 to 6 carbon atoms and 3 to 6 hydroxyl groups. Propylene glycol, propylene glycol/sorbitol mixtures, and propylene glycol/pentaerythritol mixtures are preferred such alcohols. Such preferred complexes according to the invention of an activated antiperspirant aluminum or aluminum-zirconium salt with a polyhydric alcohol are disclosed in documents U.S. Pat. No. 5,643,558 A and U.S. Pat. No. 6,245,325 A for example.

It is likewise possible within the scope of the present invention to use alkaline calcium-aluminum salts, as they are disclosed in document U.S. Pat. No. 2,571,030 A, for example, as antiperspirant aluminum salts. These salts can be obtained by reacting calcium carbonate with aluminum chlorhydroxide or aluminum chloride and aluminum powder, or by adding calcium chloride dihydrate to aluminum chlorhydroxide. However, it is likewise possible to use aluminum-zirconium complexes that are buffered with salts of amino acids, in particular with alkali and alkaline earth glycinates, as they are disclosed in document U.S. Pat. No. 4,017,599 A, for example.

The aluminum or aluminum-zirconium salts listed in the documents U.S. Pat. No. 6,245,325 A, U.S. Pat. No. 6,042,816 A, U.S. Pat. No. 6,245,325 A, U.S. Pat. No. 6,042,816 A, U.S. Pat. No. 6,245,325 A, U.S. Pat. No. 6,042,816 A, U.S. Pat. No. 6,245,325 A, U.S. Pat. No. 6,042,816 A or U.S. Pat. No. 7,105,691 A can also be used as preferred antiperspirant activated aluminum and aluminum-zirconium salts according to the invention, which are preferably stabilized by amino acids, in particular glycine, hydroxyalkanoic acids, in particular glycolic acid and lactic acid, or betaines.

Further preferred activated aluminum salts are those of the general formula $Al_2(OH)_{6-a}Xa$, where X is Cl, Br, I or $NO_3$, and "a" is a number from 0.3 to 5, especially from 0.8 to 2.5, and in particular from 1 to 2, so that the molar ratio of Al:X is 0.9:1 to 2.1:1. Such activated antiperspirant aluminum salts are disclosed in document U.S. Pat. No. 6,074,632 A, for example. Aluminum chlorohydrate (which is to say X is Cl in the aforementioned formula) is particularly preferred, and specifically 5/6 basic aluminum chlorohydrate, where "a" is 1, so that the molar ratio of aluminum to chlorine is 1.9:1 to 2.1:1.

Preferred activated aluminum-zirconium salts are those of the general formula $ZrO(OH)_{2-pb}Y_b$, where Y is Cl, Br, I, $NO_3$ or $SO_4$, b is a rational number from 0.8 to 2, and p is the valence of Y, so that the molar ratio of Al:Zr is 2 to 10, and the ratio of metal:(X+Y) is from 0.73 to 2.1, especially from 0.9 to 1.5. Such activated antiperspirant aluminum-zirconium salts are disclosed in the aforementioned document U.S. Pat. No. 6,074,632 A, for example. A particularly preferred salt is aluminum-zirconium chlorohydrate (which is to say X and Y are Cl), which has an Al:Zr ratio of 2 to 10 and a metal:Cl molar ratio of 0.9 to 2.1. Preferred active antiperspirant ingredients are disclosed in documents U.S. Pat. No. 6,663,854 A and US 2004/0009133 A1.

Antiperspirant aluminum salts that are particularly preferred according to the invention have a metal-to-chloride molar ratio of 1.9 to 2.1. The metal-to-chloride ratio of likewise particularly preferred aluminum sesquichlorohydrates within the scope of the invention is 1.5:1 to 1.8:1. Preferred aluminum-zirconium tetrachlorohydrates have a molar ratio of Al:Zr of 2 to 6 and of metal:chloride of 0.9 to 1.3, in particular salts having a metal-to-chloride molar ratio of 0.9 to 1.1, preferably of 0.9 to 1.0, being preferred.

Within the scope of the present invention, a particularly effective hydrogel formation between the compound of formula (PP-I) and the antiperspirant aluminum salts is achieved when the compound of formula (PP-I) is present in a total amount of 0.05 to 20 wt. %, especially 0.1 to 15 wt. %, preferably 0.3 to 10 wt. %, more preferably 0.5 to 7 wt. %, still more preferably 0.8 to 5 wt. %, and in particular 1 to 3 wt. %, based on the total weight of the antiperspirant cosmetic agent. It may furthermore be provided within the scope of the present invention that the compound of formula (PP-I) is present in a total amount of 0.05 to 40 wt. %, especially 0.5 to 36 wt. %, preferably 1 to 31 wt. %, more preferably 3 to 29 wt. %, still more preferably 5 to 27 wt. %, and in particular 8 to 25 wt. %, based on the total weight of the antiperspirant cosmetic agent. However, it is also possible within the scope of the invention that the antiperspirant cosmetic agents include the compound of formula (PP-I) in a total amount of 0.05 to 40 wt. %, especially 0.3 to 36 wt. %, preferably 0.5 to 30 wt. %, more preferably 0.7 to 20 wt. %, still more preferably 1.0 to 18 wt. %, and in particular 1.5 to 12 wt. %, based on the total weight of the propellant-including antiperspirant cosmetic agent. Without being limited to this theory, the use of the above-mentioned amount(s) of the compound of formula (PP-I) results in a significantly increased and extremely pH-selective hydrogel formation with the antiperspirant aluminum salt. This ensures effective clogging of the excretory ducts of the sweat glands, and consequently an outstanding antiperspirant action. The use of the above-mentioned amounts of the compound of formula (PP-I) furthermore does not result in an undesirable premature hydrogel formation in the antiperspirant cosmetic composition or on the skin surface, so that the outstanding antiperspirant action is ensured even over extended storage periods.

Particularly good results with respect to the clogging of the excretory ducts of the sweat glands through hydrogel formation are obtained when the antiperspirant cosmetic agent includes at least one compound of formula (PP-Ia)

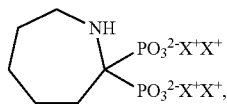

(PP-Ia)

where
X$^+$ denotes H$^+$, Li$^+$, Na$^+$, K$^+$, NH$_4^+$, ½ Mg$^{2+}$, ½ Ca$^{2+}$, ½ Mn$^{2+}$, ½ Zn$^{2+}$, ⅓ Al$^{3+}$, ¼ Zr$^{4+}$ or at least one antiperspirant aluminum salt.

The combination or mixture of acetyl cycloheptane diphosphoric acid or the salts thereof (PP-Ia) with at least one antiperspirant aluminum salt results in an extremely pH-selective enhanced hydrogel formation at pH values that are present within the excretory ducts of the sweat glands, whereby effective clogging of these excretory ducts as a result of the hydrogel formation, and consequently outstanding antiperspirant action, is ensured.

The antiperspirant action of the antiperspirant cosmetic agents according to the invention can be further improved if the antiperspirant cosmetic agent has a weight ratio of the antiperspirant aluminum salt to the compound of formula (PP-I) of 40:1 to 19:1, especially of 30:1 to 16:1, preferably of 20:1 to 15:1, more preferably of 10:1 to 13:1, still more preferably of 9:1 to 12:1, and in particular of 8:1 to 1:1. In this connection, it may also be provided that the antiperspirant cosmetic agent has a weight ratio of the antiperspirant aluminum salt to the compound of formula (PP-I) of 1:1.5 to 1:40, especially of 1:2 to 1:35, more preferably of 1:2.5 to 1:30, still more preferably of 1:3 to 1:25, and in particular of 1:3.5 to 1:20. The above-mentioned weight ratio refers to the total amount of all antiperspirant aluminum salts and the total amount of all compounds of formula (PP-I) in the antiperspirant cosmetic agent.

Within the scope of a particularly preferred embodiment, the weight ratio of the antiperspirant aluminum salt to the compound of formula (PP-I) is 1.5:1. Moreover, the use of a weight ratio of the antiperspirant aluminum salt to the compound of formula (PP-I) of 10:1 also results in antiperspirant cosmetic agents according to the invention that have an outstanding antiperspirant action. Moreover, when the above-mentioned weight ratio is used, it is also possible to use protic solvents, in particular in high concentrations or amounts, without adversely affecting the antiperspirant action of the antiperspirant cosmetic agents according to the invention, whereby extremely flexible formulating of the agents according to the invention is possible.

According to a further embodiment of the present invention, the antiperspirant cosmetic agent comprises no zirconium-containing compounds. The avoidance according to the invention of the use of zirconium-containing antiperspirant compounds, such as zirconium-aluminum mixed salts, results in the more cost-effective provision of the antiperspirant cosmetic agent according to the invention since the raw materials used to produce the zirconium-containing compounds are more expensive.

The antiperspirant cosmetic agent preferably includes free water in a total amount of less than 10 wt. %, especially of less than 8 wt. %, preferably of less than 5 wt. %, more preferably of less than 3 wt. %, still more preferably of less than 1 wt. %, and in particular 0 wt. %, based on the total weight of the antiperspirant cosmetic agent. "Free water" within the meaning of the present invention thus shall be understood to mean water that is different from constitutional water, hydration water or similarly molecularly bound water present in the components used, in particular of the antiperspirant aluminum salts.

Significantly, it was found that the clogging of the excretory ducts of the sweat glands through hydrogel formation, which takes place when at least one antiperspirant aluminum salt is combined with at least one compound of formula (PP-I), can be significantly increased if the antiperspirant cosmetic agents according to the invention include free water in an amount of 15 to 96 wt. %, based on the total weight of the antiperspirant cosmetic agent. In a particularly preferred embodiment of the present invention, the antiperspirant cosmetic agent thus includes free water in a total amount of 15 to 96 wt. %, especially of 25 to 80 wt. %, preferably of 30 to 70 wt. %, and in particular of 40 to 60 wt. %, based on the total weight of the antiperspirant cosmetic agent.

The antiperspirant cosmetic agents according to the invention are preferably present as suspensions of the undissolved antiperspirant aluminum salt in the cosmetic oil that is liquid at 20° C. and 1,013 hPa.

In a further preferred form of administration, the antiperspirant cosmetic agent is present as a water-in-oil emulsion. This may be in particular a sprayable water-in-oil emulsion, which can be sprayed by way of a propellant. In this connection, it is preferred if the antiperspirant cosmetic agent according to the invention, which is present in the form of a water-in-oil emulsion, includes the compound of formula (PP-I) in a total amount of 0.05 to 20 wt. %, especially of 0.1 to 15 wt. %, preferably of 0.3 to 10 wt. %, more preferably of 0.5 to 7 wt. %, still more preferably of 0.8 to 5 wt. %, and in particular of 1 to 3 wt. %, based on the total weight of the antiperspirant cosmetic agent.

It may also be provided within the scope of the present invention that the antiperspirant cosmetic agent is present as an oil-in-water emulsion. In this case, the agent according to the invention is preferably sprayed as a propellant-free pump spray or squeeze spray or is applied as a roll-on. In this connection, it is preferred if the antiperspirant cosmetic agent, which is present in the form of an oil-in-water emulsion, includes the compound of formula (PP-I) in a total amount of 0.05 to 20 wt. %, especially of 0.1 to 15 wt. %, preferably of 0.3 to 10 wt. %, more preferably of 0.5 to 7 wt. %, still more preferably of 0.8 to 5 wt. %, and in particular of 1 to 3 wt. %, based on the total weight of the antiperspirant cosmetic agent.

According to the invention, it may furthermore be provided that the antiperspirant cosmetic agent is present as an aqueous, aqueous-alcoholic or aqueous-glycolic solution. As a result of the combination according to the invention of an antiperspirant aluminum salt with at least one compound of formula (PP-I), it is possible to use even protic solvents, such as aqueous solutions, to formulate the antiperspirant cosmetic agents according to the invention without resulting in a significant decrease in the antiperspirant action. Adding the at least one compound of formula (PP-I) ensures effective blocking of the excretory ducts of the sweat glands, and consequently an outstanding antiperspirant action, even when protic solvents are used.

According to preferred embodiment of the present invention, the antiperspirant cosmetic agent includes ethanol in a total amount of 1 to 50 wt. %, especially of 5 to 40 wt. %, preferably of 7 to 35 wt. %, and in particular of 10 to 30 wt. %, based on the total weight of the antiperspirant cosmetic agent. However, it may also be provided that the antiperspirant cosmetic agent includes ethanol in a total amount of 10 to 95 wt. %, especially of 15 to 90 wt. %, preferably of 20 to 87 wt. %, more preferably of 30 to 85 wt. %, and in particular of 40 to 80 wt. %, based on the total weight of the antiperspirant cosmetic agent. As mentioned above, the use of the compound of formula (PP-I) allows even high amounts of protic solvents, such as ethanol, to be used, without the antiperspirant action of the antiperspirant cosmetic agent according to the invention being adversely influenced.

The antiperspirant cosmetic agent according to the invention can be applied using different methods. According to a preferred embodiment, the antiperspirant cosmetic agent is formulated as a spray application. The spray application is carried out using a spraying device, which in a container contains a filling composed of the antiperspirant cosmetic agent according to the invention in liquid, viscous-flowable, suspension or powder form. The filling can be pressurized by a propellant (pressurized cans, pressurized containers, aerosol dispensers), or it can be a pump atomizer that contains no propellant gas and is to be operated mechanically (pump sprays, squeeze bottle). The containers comprise a withdrawal device, preferably in the form of valves, allowing the content to be withdrawn in the form of a mist, smoke, foam, powder, paste or fluid jet. Especially cylindrical vessels made of metal (aluminum, tinplate, volume preferably no more than 1,000 mol), protected or shatterproof glass or plastic (volume preferably no more than 220 ml) or shattering glass or plastic (volume preferably 50 to 400 ml) can be used as containers for the spraying devices. Cream-like, gel-like, pasty and liquid agents can be packaged in pump, spray or squeeze dispensers, for example, in particular also in multi-chamber pump, multi-chamber spray, or multi-chamber squeeze dispensers. The packaging for the agents according to the invention can be opaque, but may also be transparent or translucent.

The antiperspirant cosmetic agent is preferably formulated as a stick, soft solid, cream, roll-on, dibenzylidene alditol-based gel, or loose or compact powder. The formulation of the antiperspirant cosmetic agents according to the invention in a particular form of administration, such as an antiperspirant roll-on or an antiperspirant stick or an antiperspirant gel, is preferably dependent on the requirements of the intended purpose. Depending on the intended purpose, the antiperspirant cosmetic agents according to the invention can thus be present in solid, semi-solid, liquid, disperse, emulsified, suspended, gel-like, multi-phase or powder form. The term "liquid" within the meaning of the present invention also covers any type of solid dispersions in liquids. Furthermore, multi-phase antiperspirant cosmetic agents according to the invention within the meaning of the present invention shall be understood to mean agents which contain at least two different phases having a phase separation and in which the phases may be disposed horizontally, which is to say on top of each other, or vertically, which is to say next to each other.

The application can take place by way of a roller ball applicator, for example. Such rollers comprise a ball that is mounted in a ball bed and can be moved by motion across a surface. The ball picks up a small amount of the antiperspirant cosmetic agent according to the invention to be distributed in this process and delivers the same to the surface to be treated. As described above, the packaging for the agents according to the invention can be opaque, transparent or translucent.

Moreover, it is also possible to apply the antiperspirant cosmetic agents according to the invention by way of a solid stick.

However, it may also be preferred according to the invention for the antiperspirant cosmetic agent to be present on and/or in a disposable substrate, selected from the group consisting of wipes, pads and puffs. Moist wipes, which is to say moist wipes that are prefabricated for the use, preferably packaged individually, as they are well known from the field of glass cleaning or the field of moist toilet paper, for example, are particularly preferred. Such moist wipes, which advantageously may also include preservatives, are impregnated with an antiperspirant cosmetic agent according to the invention, or have the same applied thereto, and are preferably individually packaged. They may also be used as deodorant wipes, for example, which is of particularly interest for use away from home. Preferred substrate materials are selected from porous planar wipes. They can be composed of a fibrous or cellular flexible material, which has sufficient mechanical stability and softness for use on the skin at the same time. These wipes include wipes made of woven and non-woven synthetic and natural fibers, felt, paper or foam, such as hydrophilic polyurethane foam. Preferred deodorizing or antiperspirant substrates according to the invention can be obtained by saturation or impregnation, or else by melting an antiperspirant cosmetic agent according to the invention onto a substrate.

The antiperspirant cosmetic agents according to the invention can additionally include further auxiliary substances. The antiperspirant cosmetic agents according to the invention preferably comprise at least one further auxiliary substance, selected from the group consisting of (i) emulsifiers and/or surfactants; (ii) thickeners; (iii) chelating agents; (iv) active deodorant ingredients; (v) monohydric and/or polyhydric alcohols and/or polyethylene glycols; (vi) skin-cooling active ingredients; (vii) propellants; and (viii) the mixtures thereof.

Preferably suited emulsifiers and surfactants according to the invention are selected from anionic, cationic, nonionic, amphoteric, in particular ampholytic and zwitterionic, emulsifiers and surfactants. Surfactants are amphiphilic (bifunctional) compounds, which are composed of at least one hydrophobic molecule part and at least one hydrophilic molecule part. The hydrophobic group is preferably a hydrocarbon chain having 8 to 28 carbon atoms, which can be saturated or unsaturated, linear or branched. This $C_8$ to $C_{28}$ alkyl chain is particularly preferably linear.

Anionic surfactants shall be understood to mean surfactants carrying exclusively anionic charges; they include carboxyl groups, sulfonic acid groups, or sulfate groups, for example. Particularly preferred anionic surfactants are alkyl sulfates, alkyl ether sulfates, acyl glutamates, and $C_{8-24}$ carboxylic acids, and the salts thereof, known as soaps.

Cationic surfactants shall be understood to mean surfactants carrying exclusively cationic charges; they include quaternary ammonium groups, for example. Cationic surfactants of the quaternary ammonium compound, esterquat and amidoamine types are preferred. Preferred quaternary ammonium compounds are ammonium halides and the imidazolium compounds known under the INCI names Quaternium-27 and Quaternium-83. Other cationic surfactants that can be used according to the invention are the quaternized protein hydrolysates. Preferred esterquats are quaternized ester salts of fatty acids with triethanolamine, quaternized ester salts of fatty acids with diethanol alkylamines, and quaternized ester salts of fatty acids with 1,2-dihydroxypropyl dialkylamines.

Amphoteric surfactants are divided into ampholytic surfactants and zwitterionic surfactants. Ampholytic surfactants are understood to include those surface active compounds that carry both acidic (—COOH or —SO$_3$H groups, for example) and basic hydrophilic groups (amino groups, for example) and can exhibit acidic or basic behavior, depending on the conditions. A person skilled in the art considers zwitterionic surfactants to be surfactants that carry both a negative charge and a positive charge in the same molecule. Examples of preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethyl imidazolines, each having 8 to 24 carbon atoms in the alkyl group.

Examples of preferred ampholytic surfactants are N-alkyl glycines, N-alkylaminopropionic acids, N-alkylaminobutytic acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids, each having 8 to 24 carbon atoms in the alkyl group.

The compositions according to the invention formulated as emulsions, in particular as oil-in-water emulsions, preferably include at least one nonionic oil-in-water emulsifier having an HLB value of more than 7 to 20. These are emulsifiers that are generally known to a person skilled in the art, as they are listed in Kirk-Othmer, "Encyclopedia of Chemical Technology," 3rd edition, 1979, Volume 8, pages 913-916, for example. For ethoxylated products, the HLB value is calculated according to formula HLB=(100−L):5, where L is the weight proportion of the lipophilic groups, which is to say of the fatty alkyl or fatty acyl groups, in the ethylene oxide adducts, expressed in percent by weight. In this connection, it may be preferred according to the invention if furthermore a water-in-oil emulsifier having an HLB value of greater than 1.0 and less than/equal to 7.0 is used. Suitable nonionic oil-in-water emulsifiers and suitable nonionic water-in-oil emulsifiers within the scope of the present invention are described in the German unexamined patent application DE 102006004957 A1, for example.

For thickening the antiperspirant cosmetic agents according to the invention preferably substances are used that are selected from cellulose ethers, especially hydroxyalkyl celluloses, in particular hydroxypropyl cellulose, hydroxypropyl methyl cellulose, hydroxyethyl cellulose, carboxymethyl cellulose, cetyl hydroxyethylcellulose, hydroxybutyl methyl cellulose, methyl hydroxyethyl cellulose, furthermore xanthan gum, sclerotium gum, succinoglycans, polygalactomannan gums, in particular guar gums and locust bean gum, in particular guar gum and locust bean gum itself and the nonionic hydroxyalkyl guar derivatives and locust bean gum derivatives, such as hydroxypropyl guar, carboxymethyl hydroxypropyl guar, hydroxypropyl methyl guar, hydroxyethyl guar and carboxymethyl guar, furthermore pectins, agar, caragheen (carrageenan), tragacanth, gum arabic, karaya gum, tara gum, gellan gum, gelatin, casein, propylene glycol alginate, alginic acids and the salts thereof, in particular sodium alginate, potassium alginate and calcium alginate, furthermore polyvinylpyrrolidones, polyvinyl alcohols, polyacrylamides, furthermore—albeit less preferred—physically (such as by way of pre-gelatinization) and/or chemically modified starches, in particular hydroxypropylated starch phosphates and starch octenyl succinates and the aluminum, calcium or sodium salts thereof, furthermore—likewise less preferred—acrylic acid/acrylate copolymers, acrylic acid/acrylamide copolymers, acrylic acid/vinylpyrrolidone copolymers, acrylic acid/vinylformamide copolymers, and polyacrylates. Particularly preferred thickeners are selected from cellulose ethers, especially from hydroxyalkyl celluloses, in particular from hydroxypropyl cellulose, hydroxypropyl methyl cellulose, hydroxyethyl cellulose, carboxymethyl cellulose, cetyl hydroxyethylcellulose, hydroxybutyl methyl cellulose and methyl hydroxyethyl cellulose, and mixtures thereof. The thickener used is preferably hydroxyethyl cellulose.

So as to further support the clogging of the excretory ducts of the sweat glands through the hydrogel formation when adding at least one compound of formula (PP-I), it may be advantageous to add at least one chelating agent to the antiperspirant cosmetic agents according to the invention, which is selected from ethylenediaminetetraacetic acid (EDTA) and the salts thereof, and from nitrilotriacetic acid (NTA), and mixtures of these substances, in a total amount of 0.01 to 0.5 wt. %, especially of 0.02 to 0.3 wt. %, and in particular of 0.05 to 0.1 wt. %, based on the total weight of the antiperspirant agent according to the invention. Within the scope of the present invention, however, it is also possible to use chelating agents that are selected from the group consisting of β-alanine diacetic acid, cyclodextrin, diethylenetriamine pentamethylene phosphonic acid, sodium-, potassium-, calciumdisodium-, ammonium- and triethanolamine salts of ethylenediaminetetraacetic acid (EDTA), etidronic acid, hydroxyethyl ethylenediaminetri-acetic acid (HEDTA) and the sodium salts thereof, sodium salts of nitrilotriacetic acid (NTA), diethylene triamine pentaacetic acid, phytinic acid, hydroxypropyl cyclodextrin, methyl cyclodextrin, pentasodium aminotrimethylene phosphonate, pentasodium ethylenediamine tetramethylene phosphonate, pentasodium diethylene triamine pentaacetate, pentasodium triphosphate, potassium EDTMP, sodium EDTMP, sodium dihydroxyethyl glycinate, sodium phytate, sodium polydimethylglycinophenol sulfonate, tetrahydroxy-ethyl ethylenediamine, tetrahydroxypropyl ethylenediamine, tetrapotassium etidronate, tetrasodium etidronate, tetrasodium iminodisuccinate, trisodium ethylenediamine disuccinate, and desferrioxamine.

The antiperspirant action of the antiperspirant cosmetic agents according to the invention can be further increased if at least one active deodorant ingredient is present in a total amount of 0.0001 to 40 wt. %, especially of 0.2 to 20 wt. %, preferably of 1 to 15 wt. %, and in particular of 1.5 to 5 wt. %, based on the total weight of the antiperspirant cosmetic agent according to the invention. If ethanol is used in the agents according to the invention, this is not considered an active deodorant ingredient within the scope of the present invention, but a component of the carrier. Preferred active deodorant ingredients according to the invention are selected from the group consisting of (i) silver salts; (ii) aromatic alcohols, in particular 2-benzylheptane-1-ol and mixtures of 2-benzylheptane-1-ol and phenoxyethanol; (iii) 1,2-alkane diols having 5 to 12 carbon atoms, in particular 3-(2-ethylhexyloxy)-1,2-propane diol; (iv) triethyl citrates; (v) active ingredients against exoesterases, in particular against arylsulfatase, lipase, beta-glucuronidase and cystathionine β-lyase; (vi) cationic phospholipids; (vii) odor absorbers, in particular silicates, such as montmorillonite, kaolinite, illite, beidellite, nontronite, saponite, hectorite, bentonite, smectite, and talcum, zeolites, zinc ricinoleate, cyclodextrins; (viii) deodorizingly acting ion exchangers; (ix) antimicrobial substances; (x) prebiotically active components; and (xi) mixtures of these active deodorant ingredients.

Preferred antiperspirant cosmetic agents according to the invention furthermore include at least one water-soluble polyhydric $C_{2-9}$ alkanol having 2 to 6 hydroxyl groups and/or at least one water-soluble polyethylene glycol having 3 to 50 ethylene oxide units, and mixtures thereof. These include the active deodorant ingredients not mentioned above in the form of 1,2-alkane diols. Preferred alkanols are selected from 1,2-propylene glycol, 2-methyl-1,3-propane-diol, glycerol, 1,2-butylene glycol, 1,3-butylene glycol, 1,4-butylene glycol, pentylene glycols such as 1,2-pentanediol and 1,5-pentanediol, hexanediols such as 1,2-hexanediol and 1,6-hexanediol, hexanetriols such as 1,2,6-hexanetriol, 1,2-octanediol, 1,8-octanediol, dipropylene glycol, tripropylene glycol, diglycerol, triglycerol, erythritol, sorbitol, cis-1,4-dimethylol cyclohexane, trans-1,4-dimethylol cyclohexane, arbitrary isomer mixtures of cis- and trans-1,4-dimethylol cyclohexane, and mixtures of the aforementioned substances. Suitable water-soluble polyethylene glycols are selected from PEG-3, PEG-4, PEG-6, PEG-7, PEG-8, PEG-9, PEG-10, PEG-12, PEG-14, PEG-16, PEG-18 and PEG-20, and mixtures thereof, PEG-3 to PEG-8 being preferred.

According to a further embodiment of the present invention, the antiperspirant cosmetic agents furthermore include at least one skin-cooling active ingredient. Suitable skin-cooling active ingredients according to the invention are, for example, menthol, isopulegol and menthol derivatives, such as menthyl lactate, menthyl glycolate, menthyl ethyl oxamate, menthyl pyrrolidone carboxylic acid, menthyl methyl ether, menthoxypropanediol, menthone glycerin acetal (9-methyl-6-(1-methylethyl)-1,4-dioxaspiro(4.5)decane-2-methanol), monomenthyl succinate, 2-hydroxymethyl-3,5, 5-trimethylcyclohexanol, and 5-methyl-2-(1-methylethyl) cyclohexyl-N-ethyloxamate. Menthol, isopulegol, menthyl lactate, menthoxypropanediol, menthylpyrrolidone carboxylic acid and 5-methyl-2-(1-methylethyl)cyclohexyl-N-ethyloxamate and mixtures of these substances, in particular mixtures of menthol and menthyl lactate, menthol, menthol glycolate and menthyl lactate, menthol and menthoxypropanediol, or menthol and isopulegol, are preferred as skin-cooling active ingredients.

It may furthermore be provided that a propellant is present in the antiperspirant cosmetic agents according to the invention. In this case, they are formulated as a propellant gas-driven aerosol. Preferred propellants (propellant gases) are propane, propene, n-butane, iso-butane, iso-butene, n-pentane, pentene, iso-pentane, iso-pentene, methane, ethane, dimethylether, nitrogen, air, oxygen, nitrous oxide, 1,1,1,3-tetrafluoroethane, heptafluoro-n-propane, perfluoroethane, monochlorodifluoromethane, 1,1-difluoroethane, tetrafluoropropene, and more particularly both individually and in the mixtures thereof. It is also possible to advantageously use hydrophilic propellants, such as carbon dioxide, within the meaning of the present invention if the proportion of hydrophilic gases is selected to be low, and lipophilic propellant (such as propane/butane) is present in excess. Propane, n-butane, iso-butane and mixtures of these propellants are particularly preferred. It has been shown that the use of n-butane as the sole propellant may be particularly preferred according to the invention. The total amount of propellants is 20 to 95 wt. %, especially 30 to 85 wt. %, and in particular 40 to 75 wt. %, in each case based on the total weight of the antiperspirant, composed of the antiperspirant cosmetic agent according to the invention and the propellant. In this connection, it may also be provided that the total amount of propellant is 1 to 95 wt. %, especially 2 to 85 wt. %, and in particular 3 to 75 wt. %, in each case based on the total weight of the antiperspirant, composed of the antiperspirant cosmetic agent according to the invention and the propellant.

Furthermore, lipophilic thickeners can be used according to the invention as auxiliary substances. The at least one antiperspirant aluminum salt is preferably suspended undissolved in at least one cosmetic oil that is liquid at 20° C. and 1,013 hPa. To improve applicability, at least one lipophilic thickener can also be added to this suspension as a suspending aid. Preferred lipophilic thickeners according to the invention are selected from hydrophobized clay minerals and fumed silica.

In a preferred embodiment, the antiperspirant cosmetic agents according to the invention are characterized by being formulated as water-in-oil emulsions and including—based on the total weight of the antiperspirant cosmetic agent according to the invention— at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;

at least one compound of formula (PP-I) in a total amount of 0.05 to 20 wt. %, especially 0.1 to 15 wt. %, preferably 0.3 to 10 wt. %, more preferably 0.5 to 7 wt. %, still more preferably 0.8 to 5 wt. %, and in particular 1 to 3 wt. %;

12 to 90% by weight, especially 25 to 55% by weight, preferably 30 to 50% by weight, and in particular 35 to 45 wt. % water;

at least one emulsifier; and at least one substance selected from the group consisting of cosmetic oils that are liquid at 20° C. and 1,013 hPa, odorous substances and waxes.

In a further preferred embodiment, the antiperspirant cosmetic agents according to the invention are characterized by being formulated as oil-in-water emulsions and including—based on the total weight of the antiperspirant cosmetic agent according to the invention— at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;

at least one compound of formula (PP-I) in a total amount of 0.05 to 20 wt. %, especially 0.1 to 15 wt. %, preferably 0.3 to 10 wt. %, more preferably 0.5 to 7 wt. %, still more preferably 0.8 to 5 wt. %, and in particular 1 to 3 wt. %;

15 to 90% by weight, especially 25 to 55% by weight, preferably 30 to 50% by weight, and in particular 35 to 45 wt. % water;

at least one emulsifier; and at least one substance selected from the group consisting of cosmetic oils that are liquid at 20° C. and 1,013 hPa, odorous substances and waxes.

A further preferred embodiment of the present invention comprises antiperspirant cosmetic agents according to the invention, which are characterized by including—based on the total weight of the antiperspirant cosmetic agent according to the invention— at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;

at least one compound of formula (PP-I) in a total amount of 0.05 to 20 wt. %, especially 0.1 to 15 wt. %, preferably 0.3 to 10 wt. %, more preferably 0.5 to 7 wt. %, still more preferably 0.8 to 5 wt. %, and in particular 1 to 3 wt. %;

15 to 90% by weight, especially 25 to 80% by weight, preferably 30 to 75% by weight, and in particular 40 to 60 wt. % water; and 0.01 to 2% by weight, especially 0.1 to 1% by weight, preferably 0.2 to 0.7% by weight, and in particular 0.3 to 0.5 wt. % of a thickener.

A further preferred embodiment of the present invention comprises antiperspirant cosmetic agents according to the invention, which are characterized by including—based on the total weight of the antiperspirant cosmetic agent according to the invention— at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;

at least one compound of formula (PP-I) in a total amount of 0.05 to 20 wt. %, especially 0.1 to 15 wt. %, preferably 0.3 to 10 wt. %, more preferably 0.5 to 7 wt. %, still more preferably 0.8 to 5 wt. %, and in particular 1 to 3 wt. %;

15 to 90% by weight, especially 25 to 80% by weight, preferably 30 to 75% by weight, and in particular 40 to 60 wt. % water; and 0.01 to 2% by weight, especially 0.1 to 1% by weight, preferably 0.2 to 0.7% by weight, and in particular 0.3 to 0.5 wt. % of a thickener, wherein the antiperspirant cosmetic agents according to the invention have a dynamic viscosity in the range from 10 to 5000 mPas, especially from 100 to 1000 mPas, preferably from 200 to 800 mPas, measured by way of a Brookfield viscometer, RV 4 spindle, 20 s$^{-1}$, without Helipath, at an ambient temperature of 20° C. and a sample temperature of 20° C.

A further preferred embodiment of the present invention comprises antiperspirant cosmetic agents according to the invention, which are characterized by including—based on the total weight of the antiperspirant cosmetic agent according to the invention— at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;

at least one compound of formula (PP-I) in a total amount of 0.05 to 8 wt. %, especially 0.1 to 7 wt. %, preferably 0.3 to 5 wt. %, more preferably 0.5 to 3 wt. %, still more preferably 0.8 to 2.5 wt. %, and in particular 1 to 2 wt. %;

15 to 90 wt. %, especially 25 to 80 wt. %, preferably 30 to 75 wt. %, and in particular 40 to 60 wt. % water; and 0.01 to 2% by weight, especially 0.1 to 1% by weight, preferably 0.2 to 0.7% by weight, and in particular 0.3 to 0.5 wt. % of a thickener, wherein the antiperspirant cosmetic agents according to the invention have a dynamic viscosity in the range from 1,000 to 800,000 mPas, especially from 2,000 to 700,000 mPas, preferably from 3,000 to 500,000 mPas, measured by way of a Brookfield viscometer, RV 4 spindle, 20 s$^{-1}$, without Helipath, at an ambient temperature of 20° C. and a sample temperature of 20° C.

In another preferred embodiment, the antiperspirant cosmetic agents according to the invention are characterized by being formulated as water-in-oil emulsions and including—based on the total weight of the antiperspirant cosmetic agent according to the invention— at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;

at least one compound of formula (PP-I) in a total amount of 0.05 to 20 wt. %, especially 0.1 to 15 wt. %, preferably 0.3 to 10 wt. %, more preferably 0.5 to 7 wt. %, still more preferably 0.8 to 5 wt. %, and in particular 1 to 3 wt. %;

15 to 75% by weight, especially 25 to 60% by weight, preferably 30 to 55% by weight, and in particular 35 to 50 wt. % water.

In a further preferred embodiment, the antiperspirant cosmetic agents according to the invention are characterized by being formulated as oil-in-water emulsions and including—based on the total weight of the antiperspirant cosmetic agent according to the invention—
- at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;
- at least one compound of formula (PP-I) in a total amount of 0.05 to 20 wt. %, especially 0.1 to 15 wt. %, preferably 0.3 to 10 wt. %, more preferably 0.5 to 7 wt. %, still more preferably 0.8 to 5 wt. %, and in particular 1 to 3 wt. %;
- 15 to 90 wt. %, especially 25 to 80 wt. %, preferably 30 to 75 wt. %, and in particular 40 to 60 wt. % water; and
- optionally 0.01 to 2% by weight, especially 0.1 to 1% by weight, preferably 0.2 to 0.7% by weight, and in particular 0.3 to 0.5 wt. % of a thickener.

It may also be provided within the scope of the present invention to formulate the cosmetic agent according to the invention as a two-component agent. The individual components are preferably stored in separate containers for this purpose and consecutively applied to the skin in any arbitrary order. Cosmetic agents according to the invention can therefore be present as kit-of-parts, comprising—separately from each other—
 a) at least one first container containing a cosmetic agent comprising at least one antiperspirant aluminum-containing compound; and
 b) at least one second container containing a cosmetic agent comprising at least one compound of formula (PP-I), wherein the cosmetic agent includes less than 0.5 wt. %, especially less than 0.2 wt. %, preferably less than 0.05 wt. %, more preferably less than 0.005 wt. %, and in particular 0 wt. % aluminum-containing compounds.

The term "aluminum-containing compounds" within the scope of the present invention shall be understood to mean antiperspirant aluminum salts and aluminum-zirconium salts.

The present invention further relates to the use of a combination of at least one substance, selected from the group consisting of cosmetic oils that are liquid at 20° C. and 1,013 hPa, odorous substances and waxes, at least one antiperspirant aluminum salt in a total amount of 0.1 to 80 wt. %, based on the total weight of the combination, and at least one compound of formula (PP-I),

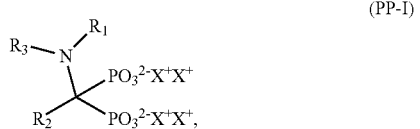
(PP-I)

where
R$^1$ denotes hydrogen or a linear or branched alkyl group having 1 to 6 carbon atoms,
R$^2$ and R$^3$, each independently of one another, denote a linear or branched alkyl group having 1 to 6 carbon atoms, or R$^2$ and R$^3$ form a cyclic group having 4 to 8 carbon atoms and optionally one heteroatom, selected from the group consisting of N, O, and S, and
X$^+$ denotes H$^+$, Li$^+$, Na$^+$, K$^+$, NH$_4^+$, ½ Mg$^{2+}$, ½ Ca$^{2+}$, ½ Mn$^{2+}$, ½ Zn$^{2+}$, ⅓ Al$^{3+}$, ¼ Zr$^{4+}$ or at least one antiperspirant aluminum salt for reducing and/or preventing perspiration. The term "combination" within the meaning of the present invention also comprises a mixture of the at least one substance and of the antiperspirant aluminum salt with the at least one compound of formula (PP-I). What was said with respect to the antiperspirant cosmetic agents according to the invention applies, mutatis mutandis, to the use of the above-mentioned combination.

The present invention further relates to a non-therapeutic cosmetic method for preventing and/or reducing perspiration of the body, in which an antiperspirant cosmetic agent, including at least one substance selected from the group consisting of cosmetic oils that are liquid at 20° C. and 1,013 hPa, odorous substances and waxes, at least one antiperspirant aluminum salt in a total amount of 0.1 to 80 wt. %, based on the total weight of the antiperspirant cosmetic agent, and at least one compound of formula (PP-I), is applied to the skin, and more particularly to the skin of the axilla region.

However, it may also be provided within the scope of the method according to the invention that first a cosmetic agent including an antiperspirant aluminum salt and thereafter an aluminum salt-free cosmetic agent, including at least one compound of formula (PP-I) are applied. However, it is also possible to first apply the aluminum salt-free cosmetic agent, including at least one compound of formula (PP-I), and thereafter use a cosmetic agent including an antiperspirant aluminum salt. The time period between the applications of the two agents is 10 seconds to 24 hours. What was said with respect to the antiperspirant cosmetic agents according to the invention and the use according to the invention applies, mutatis mutandis, to the method according to the invention.

Finally, the present invention moreover relates to the use of at least one compound of formula (PP-I)

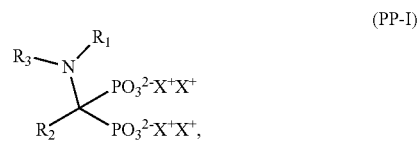
(PP-I)

where
R$^1$ denotes hydrogen or a linear or branched alkyl group having 1 to 6 carbon atoms,
R$^2$ and R$^3$, each independently of one another, denote a linear or branched alkyl group having 1 to 6 carbon atoms, or R$^2$ and R$^3$ form a cyclic group having 4 to 8 carbon atoms and optionally one heteroatom, selected from the group consisting of N, O, and S, and
X$^+$ denotes H$^+$, Li$^+$, Na$^+$, K$^+$, NH$_4^+$, ½ Mg$^{2+}$, ½ Ca$^{2+}$, ½ Mn$^{2+}$, ½ Zn$^{2+}$, ⅓ Al$^{3+}$, ¼ Zr$^{4+}$ or at least one antiperspirant aluminum salt for enhancing the blocking of the sweat gland(s) and/or for blocking the sweat gland(s).

"Blocking the sweat gland(s)" according to the invention shall be understood to mean the formation of a hydrogel and/or precipitate of the at least one antiperspirant aluminum salt and the at least one compound of formula (PP-I) in the excretory duct of the sweat gland, or in the excretory ducts of the sweat glands. However, "blocking" within the meaning of the present invention shall also be understood to mean supporting the formation of a precipitate of the antiperspirant aluminum salt as a result of the addition of the compound of formula (PP-I). This blocking prevents or reduces a secretion of sweat from the excretory duct. What was said with respect to the antiperspirant cosmetic agents according to the invention applies, mutatis mutandis, to the use according to the invention of the compound of formula (PP-I).

It is furthermore likewise possible within the scope of the present invention to dry a liquid mixture of the at least one antiperspirant aluminum salt with the at least one compound of formula (PP-I). This mixture can be dried, for example, by way of conventional drying methods, such as spray drying. The powders thus obtained keep excellently and have a long shelf life. The following examples describe the present invention in more detail, without limiting it to these examples.

EXAMPLES

1. Hydrogel Formation

The hydrogel formation when adding the compound of formula (PP-IA), where $X^+$=H, to a solution including an antiperspirant aluminum salt is determined as follows:

100 ml demineralized water is charged into a beaker glass, and then 35 ml of a dilution of the solution indicated in Table 1 is added. The solutions from Table 1 are diluted for this purpose in a beaker glass to an aluminum salt content of 1.25 wt. %. Thereafter, the pH value of the solution in the beaker glass is set to a pH of 6.5 to 6.6 by adding a 2% sodium bicarbonate solution while stirring. Immediately after the pH value has been set, the turbidity of the solution is measured using a Methrom Optrode 6.1115.000 at a wavelength of 574 nm (green-yellow) in mV (resolution 0.1 mV). The higher the turbidity of the solution, the lower is the resultant measured value in mV. Every measurement is carried out twice and the mean value therefrom is created. Turbidity is a measure of the potential of the mixture to form a hydrogel.

TABLE 1

Solutions for the turbidity measurement (information in wt. %)

|  | V-I | E-I* |
|---|---|---|
| Aluminum chlorohydrate (ACH) | 10 | 10 |
| Compound of formula (PP-Ia) where $X^+$ = H | — | 2 |

*according to the invention

The difference Δturbidity between the turbidity of comparison solution V-I and the turbidity of Example E-I according to the invention (Δturbidity [mV]=turbidity V-I–turbidity E-I) is 34 mV.

At a pH of 6.5 to 6.6, adding the compound of formula (PP-I), where $X^+$=H, results in significantly higher turbidity or hydrogel formation in sample E-I according to the invention than in comparison sample V-I. Adding the compound of formula (PP-Ia), where $X^+$=H, thus enhances the hydrogel formation and ensures effective blocking of the excretory ducts of the sweat glands.

2. Formulations

The compound of formula (PP-I) used in the following examples is preferably acetylcycloheptane diphosphoric acid or the salts thereof (formula PP-Ia), and the mixtures thereof.

Antiperspirant cosmetic agents according to the invention (quantity information in wt. %)

|  | 1 | 2 | 3 | 4 | 5 | 6 |
|---|---|---|---|---|---|---|
| Hydrogenated castor oil | — | — | — | 1.5 | 1.5 | 1.5 |
| Stearyl alcohol | 24.0 | 24.0 | 24.0 | 18 | 18 | 18 |
| Novata AB | — | — | — | 4 | 4 | 4 |
| Powder made of ACH and compound of formula (PP-I) (spray-dried, contains 10 wt. % (PP-I)) | 15.00 | 22.0 | 20.0 | 11.6 | 15.6 | 12.6 |
| Al—Zr pentachlorohydrex Gly | 7.00 | — | — | 6.00 | — | — |
| PPG-14 butyl ether | 10.0 | 10.0 | 10.0 | 15.3 | 15.3 | 15.3 |
| Hardened castor oil (e.g., Cutina HR) | 3.0 | 3.0 | 3.0 | — | — | — |
| Myristyl myristate | 1.5 | 1.5 | 1.5 | — | — | — |
| DL menthol | 0.2 | 0.2 | 0.2 | — | — | — |
| Eucalyptol | 0.2 | 0.2 | 0.2 | — | — | — |
| Anethol | 0.2 | 0.2 | 0.2 | — | — | — |
| Silica dimethyl silylate | 1.4 | 1.4 | 1.4 | — | — | — |
| Silica | 0.3 | 0.3 | 0.3 | — | — | — |
| Talcum | — | — | — | 3 | 3 | 3 |
| Emulgin B1 | — | — | — | 3 | 3 | 3 |
| Perfume | 2.0 | 2.0 | 2.0 | 1 | 1 | 1 |
| Cyclomethicone (at least 95 wt. % cyclepentasiloxane) | up to 100 | up to 100 | up to 100 | up to 100 | up to 100 | up to 100 |

Antiperspirant cosmetic agents according to the invention in the form of an oil-in-water emulsion (quantity information in wt. %)

|  | 7 | 8 |
|---|---|---|
| Cutina ® AGS | 2.5 | 2.5 |
| Cutina ® FS45 | 3.5 | 3.5 |
| Eumulgin ® B2 | 0.8 | 0.8 |
| Eumulgin ® B3 | 0.8 | 0.8 |
| Diisopropyl adipate | 6.0 | 6.0 |
| Novata ® AB | 4.0 | 4.0 |
| Cutina ® CP | 5.0 | 5.0 |
| Cutina ® HR | 4.0 | 4.0 |
| Kester Wax K62 | 5.0 | 5.0 |
| Locron ® L (ACH solution 50%) | 40 | 40 |
| Talcum Pharma G | 10 | 10 |
| Perfume | 1.2 | 1.2 |
| 2-benzylheptane-1-ol | — | 0.3 |
| Sensiva SC 50 | 0.6 | 0.6 |
| Compound of formula (PP-I) | 2.0 | 3.0 |
| 1,2-propanediol | 10 | 10 |
| Water, demineralized | up to 100 | up to 100 |

Antiperspirant cosmetic agents according to the invention in the form of microemulsions (information in wt. %)

|  | 9 | 10 | 11 | 12 |
|---|---|---|---|---|
| Plantaren ® 1200 | 1.7 | 1.7 | — | — |
| Plantaren ® 2000 | 1.1 | 1.4 | 2.4 | 2.4 |
| Glycerol monooleate | 0.71 | 0.71 | — | — |
| Dioctyl ether | 4.0 | 4.0 | 0.090 | 0.090 |
| Octyldodecanol | 1.0 | 1.0 | 0.020 | 0.020 |
| Perfume oil | 1.0 | 1.0 | 1.0 | 1.0 |
| Aluminum chlorohydrate | 8.0 | 5.0 | 5.0 | 5.0 |
| 1,2-propylene glycol | 5.0 | 5.0 | — | — |
| Glycerol | — | — | 5.0 | 5.0 |
| 2-benzylheptane-1-ol | 0.50 | — | — | — |
| Triethyl citrate | — | 0.50 | 0.50 | 0.50 |
| Triclosan | 0.10 | — | — | — |
| Compound of formula (PP-I) | 1.0 | 2.0 | 2.5 | 0.5 |
| Water | up to 100 | up to 100 | up to 100 | up to 100 |

Antiperspirant cosmetic agents according to the invention in the form of roll-ons (quantity information in wt. %)

|                                                      | 13        | 14        | 15        | 16        |
|------------------------------------------------------|-----------|-----------|-----------|-----------|
| Ethanol 96% (DEP denatured)                          | 30        | 30        | 28        | 28        |
| Mergital ® CS 11                                     | 2.0       | 2.0       | —         | —         |
| Eumulgin ® B3                                        | 2.0       | 2.0       | 2.0       | 2.0       |
| Eumulgin ® B1                                        | —         | —         | 2.0       | 2.0       |
| Aluminum chlorohydrate 50% (Locron L)                | —         | 20        | —         | 16        |
| Al—Zr pentachlorohydrex Gly                          | 20        | —         | 16        | —         |
| Hydroxyethyl cellulose                               | 0.50      | 0.50      | 0.30      | 0.30      |
| Compound of formula (PP-I)                           | 2.5       | 0.50      | 2.0       | 1.5       |
| EDTA                                                 | —         | —         | —         | 0.050     |
| Cocamidopropyl PG dimonium chloride phosphate        | 0.20      | —         | —         | —         |
| Perfume oil                                          | 0.80      | 0.80      | 1.0       | 1.0       |
| Water                                                | up to 100 | up to 100 | up to 100 | up to 100 |

Antiperspirant Wipes (Examples No. 17 to 20)

For the embodiment according to the invention as an antiperspirant wipe, 75 g of exemplary emulsions 13 and 14, or 75 g of exemplary compositions 9 and 10, was applied respectively per square meter to a single-ply substrate made of 100% viscose having a weight per unit area of 50 g/m$^2$, the substrate was cut into wipes of a suitable size and packaged into sachets.

Antiperspirant cosmetic agents according to the invention in the form of a water-in-oil emulsion (quantity information in wt. %)

|                                                         | 21        | 22        | 23        |
|---------------------------------------------------------|-----------|-----------|-----------|
| Aluminum chlorohydrate 50% in water (Locron L)          | 35.6      | 35.6      | 20.0      |
| 1,2-propylene glycol                                    | 13.0      | 13.0      | 13.0      |
| Cyclohexasiloxane                                       | 6.00      | 6.00      | 6.00      |
| Finsolv TN                                              | 8.00      | 8.00      | 8.00      |
| Abil EM 90                                              | 1.20      | 1.20      | 1.20      |
| Polyethylene wax (MW = 500 g/mol, melting pt = 83 to 91° C.) | 10.0 | 10.0 | 10.0 |
| Polyalphaolefin wax (MW = 1800 g/mol, melting pt = 41° C.)  | 0.100 | 0.100 | 0.100 |
| Compound of formula (PP-I)                              | 2.00      | 0.500     | 1.00      |
| EDTA                                                    | —         | 0.0500    | 0.0500    |
| Water                                                   | up to 100 | up to 100 | up to 100 |
| Perfume                                                 | 1.00      | 1.00      | 1.00      |

Antiperspirant cosmetic agents according to the invention (quantity information in wt. %)

|                                                | 24   | 25    |
|------------------------------------------------|------|-------|
| Cyclopentasiloxane                             | 14.0 | 14.0  |
| Abil EM 97                                     | 3.00 | 3.00  |
| Ethanol 96%                                    | 10.0 | 10.0  |
| Aluminum chlorohydrate 50% in water (Locron L) | 40.0 | 40.0  |
| 1,2-propylene glycol                           | 20.3 | 20.3  |
| Water                                          | 11.6 | 11.6  |
| Compound of formula (PP-I)                     | 2.00 | 0.500 |
| EDTA                                           | —    | 0.0750|
| Perfume                                        | 1.00 | 1.00  |

Antiperspirant cosmetic agents according to the invention (quantity information in wt. %, based on the total weight of the propellant-free composition)

|                             | 26    | 27    | 28    | 29    |
|-----------------------------|-------|-------|-------|-------|
| Aluminum chlorohydrate (ACH)| 28.6  | 14.29 | 32.11 | 28.57 |
| Bentone 38 V CG             | 5.00  | 3.93  | 4.00  | 5.00  |
| Propylene carbonate         | 1.50  | 0.71  | 1.50  | 1.80  |
| Fragrance                   | 7.14  | 6.50  | 5.00  | 6.50  |
| 2-ethylhexyl palmitate      | —     | 73.57 | —     | —     |
| Abil K 4                    | 48.4  | —     | —     | —     |
| Isopropyl myristate         | 7.37  | —     | 10.00 | 19.22 |
| Triethyl citrate            | —     | —     | 10.5  | 19.2  |
| C10-C13 isoalkane           | —     | —     | 35.39 | 19.21 |
| Compound of formula (PP-I)  | 2.00  | 1.00  | 1.50  | 0.500 |

Exemplary compositions 26 to 29 were bottled in an aluminum spray can, optionally coated with epoxy-phenolic lacquer, at a weight ratio of the propellant (butane/propane/isobutane mixture) to the suspension of 80:20 and 85:15 and 60:40 and 90:10.

Antiperspirant cosmetic agents according to the invention (quantity information in wt. %, based on the total weight of the propellant-free composition)

|                                | 30        | 31        | 32        |
|--------------------------------|-----------|-----------|-----------|
| Aluminum chlorohydrate (ACH)   | 33.0      | 33.0      | 33.0      |
| $C_{10}$ to $C_{13}$ isoalkane | 8.90      | 8.90      | 8.90      |
| Dow Corning ES-5227 DM         | 1.40      | 1.40      | 1.40      |
| Isoceteth-20                   | 0.500     | 0.500     | 0.500     |
| Dimethicone                    | 4.20      | 4.20      | 4.20      |
| Isopropyl myristate            | 9.00      | 9.00      | 9.00      |
| 1,2-propanediol                | 7.00      | 25.00     | 25.0      |
| Phenoxyethanol                 | 0.500     | 0.500     | 0.500     |
| Perfume                        | 2.50      | 2.50      | 2.50      |
| Compound of formula (PP-I)     | 2.00      | 0.500     | 1.50      |
| L-Menthol                      | 0.400     | 0.300     | —         |
| trans-anethol                  | —         | 0.300     | —         |
| Eucalyptol                     | —         | 0.300     | —         |
| Water                          | up to 100 | up to 100 | up to 100 |

Exemplary compositions 30 to 32 were bottled in an aluminum spray can, optionally coated with epoxy-phenolic lacquer, at a weight ratio of the propellant (butane/propane/isobutane mixture) to the suspension of 80:20 and 85:15 and 60:40 and 90:10.

Antiperspirant cosmetic agents according to the invention in the form of O/W emulsions (quantity information in wt. %)

|                              | 33    | 34    | 35    |
|------------------------------|-------|-------|-------|
| Aluminum chlorohydrate (ACH) | 13.0  | 13.0  | 13.0  |
| Brij S 2                     | 2.50  | 2.50  | 2.50  |
| Brij S 721                   | 1.50  | 1.50  | 1.50  |
| Perfume                      | 1.10  | 1.10  | 1.10  |
| Arlamol E                    | 0.500 | 0.500 | 0.500 |
| Bisabolol                    | 0.100 | 0.100 | 0.100 |
| Dry Flo PC                   | 0.100 | 0.100 | 0.100 |
| Compound of formula (PP-I)   | 2.00  | 3.00  | 1.00  |
| Dow Corning 2501 Cosmetic Wax| 0.100 | 0.100 | 0.100 |

-continued

|  | 33 | 34 | 35 |
|---|---|---|---|
| Tocopheryl acetate | 0.100 | 0.100 | 0.100 |
| Water | up to 100 | up to 100 | up to 100 |

Antiperspirant cosmetic agents according to the invention (quantity information in wt. %, based on the total weight of the propellant-free composition)

|  | 36 | 37 | 38 | 39 |
|---|---|---|---|---|
| Aluminum chlorohydrate (ACH) | 33.0 | 33.0 | 33.0 | 33.0 |
| Cyclomethicone | 12.0 | 9.40 | — | — |
| $C_{10}$ to $C_{13}$ isoalkane | — | — | 9.40 | 8.90 |
| Dow Corning ES-5227 DM | — | 1.40 | 1.40 | 1.40 |
| Abil EM 90 | 3.00 | — | — | — |
| Brij IC 20 | — | — | — | 0.500 |
| Dimethicone | — | 4.20 | 4.20 | 4.20 |
| Isopropyl myristate | 9.00 | 9.00 | 9.00 | 9.00 |
| Compound of formula (PP-I) | 2.50 | 1.00 | 3.00 | 0.500 |
| 1,2-propanediol | 7.00 | 7.00 | 7.00 | 7.00 |
| Phenoxyethanol | 0.500 | 0.500 | 0.500 | 0.500 |
| Perfume | 2.50 | 2.50 | 2.50 | 2.50 |
| Water | up to 100 | up to 100 | up to 100 | up to 100 |

Exemplary compositions 36 to 39 were bottled in an aluminum spray can, optionally coated with epoxy-phenolic lacquer, at a weight ratio of the propellant (butane/propane/isobutane mixture) to the suspension of 80:20 and 85:15 and 60:40 and 90:10.

Antiperspirant cosmetic agents according to the invention in the form of W/O emulsions (quantity information in wt. %)

|  | 40 | 41 | 42 | 43 |
|---|---|---|---|---|
| Aluminum chlorohydrate 50% (Locron L) | 62.5 | 62.5 | 60.0 | 58.0 |
| Propylene glycol | 5.00 | 5.00 | 7.50 | 9.50 |
| $C_{12}$ to $C_{15}$ alkylbenzoate | 8.04 | 8.04 | 8.04 | 8.04 |
| Dimethicone 2 cst | 6.43 | 6.43 | 6.43 | 6.43 |
| Dimethicone 5 cst | 1.57 | 1.57 | 1.57 | 1.57 |
| Polyethylene | 10.2 | 11.7 | 9.70 | 12.2 |
| Abil EM 90 | 0.998 | 0.998 | 0.998 | 0.998 |
| Abil EM 97 | 1.22 | 1.22 | 1.22 | 1.22 |
| Compound of formula (PP-I) | 2.50 | 1.00 | 3.00 | 0.500 |
| Synthetic wax | 0.100 | 0.100 | 0.100 | 0.100 |
| Perfume | 1.50 | 1.50 | 1.20 | 1.50 |

The following commercial products were used:

| Commercial product | INCI | Supplier/Manufacturer |
|---|---|---|
| Abil EM 90 | CETYL PEG/PPG-10/1 Dimethicone | Evonik |
| Abil EM 97 | Bis-PEG/PPG-14/14 Dimethicone, Cyclomethicone | Evonik |
| Abil K 4 | Cyclomethicone | Goldschmidt |
| Arlamol E | PPG-15 Stearyl ether | Croda |
| Bentone 38 V CG | Disteardimonium Hectorite | Elementis Specialities |
| Brij IC 20 | Isoceteth-20 | Croda |
| Brij S 2 | Steareth-2 | Croda |
| Brij S 721 | Steareth-21 | Croda |
| Cutina ® CP | Cetyl Palmitate | BASF |
| Cutina ® FS45 | Palmitic Acid, Stearic Acid | BASF |
| Cutina ® HR | Hydrogenated Castor Oil | BASF |
| Dow Dorning ® 245 | Cyclopentasiloxan | Dow Corning |
| Dow Corning ® 2501 | Bis-PEG-18 Methyl ether dimethyl silane | Dow Corning |
| Dow Corning ES-5227 DM | Dimethicone, PEG/PPG-18/18 Dimethicone at a weight ratio of 3:1 | Dow Corning |
| Dry Flo PC | Aluminum Starch Octenylsuccinate | National Starch |
| Eumulgin ® B1 | Ceteareth-12 | BASF |
| Eumulgin ® B2 | Ceteareth-20 | BASF |
| Eumulgin ® B3 | Ceteareth-30 | BASF |
| Kester Wax K62 | Cetearyl Behenate | Koster Keunen |
| Finsolv TN | C12-15 Alkyl Benzoate | Innospec |
| Locron L (AS = 50%) | Aluminum Chlorohydrate | Clariant |
| Mergital ® CS 11 | Ceteareth-11 | BASF |
| Novata ® AB | Cocoglycerides (melting point 30-32° C.) | BASF |
| Plantaren ® 1200 | LAURYL GLUCOSIDE, approx. 50% AS | BASF |
| Plantaren ® 2000 | DECYL GLUCOSIDE, approx. 50% AS | BASF |
| Sensiva ® SC 50 | 2-Ethylhexylglycerin ether | Schülke & Mayr |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An antiperspirant cosmetic agent, comprising:
   a) at least one substance selected from the group consisting of cosmetic oils which are liquid at 20° C. and 1013 hPa, odorants, and waxes;
   b) at least one antiperspirant aluminum salt in a total amount of 0.1 to 80 wt %, based on the total weight of the antiperspirant cosmetic agent, and
   c) at least one compound of formula (PP-I)

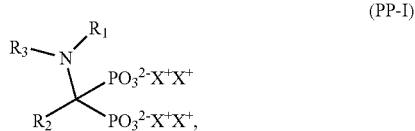

where
R$^1$ denotes hydrogen or a linear or branched alkyl group having 1 to 6 carbon atoms,
R$^2$ and R$^3$, each independently of one another, denote a linear or branched alkyl group having 1 to 6 carbon atoms, or R$^2$ and R$^3$ form a cyclic group having 4 to 8 carbon atoms and optionally one heteroatom, selected from the group consisting of N, O, and S, and
X$^+$ denotes H$^+$, Na$^+$, K$^+$, NH$_4^+$, ½ Mg$^{2+}$, ½ Ca$^{2+}$, ½ Mn$^{2+}$, ½ Zn$^{2+}$, ⅓ Al$^{3+}$, ¼ Zr$^{4+}$ or at least one antiperspirant aluminum salt,
wherein the weight ratio of the antiperspirant aluminum salt to the compound of formula (PP-I) is 8:1 to 1:1.

2. The antiperspirant cosmetic agent according to claim 1, wherein the at least one substance (a) is an odorant and comprises 0.00001 to 10% by weight based on the total weight of the antiperspirant cosmetic agent.

3. The antiperspirant cosmetic agent according to claim 1, wherein the at least one substance (a) is a wax and comprises 0.01 to 20% by weight based on the total weight of the antiperspirant cosmetic agent.

4. The antiperspirant cosmetic agent according to claim 1, wherein the at least one substance (a) is a cosmetic oil which is liquid at 20° C. and 1013 hPa, said cosmetic oil being selected from the group consisting of volatile cyclic silicone oils, volatile nonsilicone oils, nonvolatile silicone oils, nonvolatile nonsilicone oils, and mixtures thereof.

5. The antiperspirant cosmetic agent according to claim 4, wherein the cosmetic oil includes a volatile cyclic silicone oils selected from the group consisting of cyclotrisiloxane, cyclotetrasiloxane, cyclopentasiloxane, and cyclohexasiloxane, and linear silicone oils having 2 to 10 siloxane units.

6. The antiperspirant cosmetic agent according to claim 5, wherein the linear silicone oils having 2 of 10 siloxane units are selected from the group consisting of hexamethyldisiloxane, octamethyltrisiloxane, and decamethyltetrasiloxane.

7. The antiperspirant cosmetic agent according to claim 4, wherein the cosmetic oil includes a volatile nonsilicone oils selected from the group consisting of liquid paraffin oils and isoparaffin oils.

8. The antiperspirant cosmetic agent according to claim 7, wherein the cosmetic oil is selected from the group consisting of isodecane, isoundecane, isododecane, isotridecane, isotetradecane, isopentadecane, isohexadecane, and isoeicosane.

9. The antiperspirant cosmetic agent according to claim 4, wherein the cosmetic oil is a high molecular linear polyalkylsiloxane.

10. The antiperspirant cosmetic agent according to claim 4, wherein the cosmetic oil is selected from the group consisting of esters of linear or branched, saturated or unsaturated C$_{2-30}$ fatty alcohols with linear or branched, saturated or unsaturated C$_{2-30}$ fatty acids, which may be hydroxylated, the C$_8$-C$_{22}$ fatty alcohol esters of monovalent or polyvalent C$_2$-C$_7$ hydroxycarboxylic acids, the triethyl citrates, the branched saturated or unsaturated C$_{6-30}$ fatty alcohols, the mono-, di-, and triglycerides of linear or branched, saturated or unsaturated, optionally hydroxylated C$_{8-30}$ fatty acids, the dicarboxylic acid esters of linear or branched C$_2$-C$_{10}$ alkanols, the addition products of ethylene oxide and/or propylene oxide with monohydric or polyhydric C$_{3-22}$ alkanols, which may optionally be esterified, the symmetrical, asymmetrical, or cyclic esters of carbonic acid with fatty alcohols, the esters of dimers of unsaturated C$_{12-22}$ fatty acids with monohydric linear, branched, and cyclic C$_{2-18}$ alkanols or C$_{2-6}$ alkanols, the benzoic acid esters of linear or branched C$_{8-22}$ alkanols, the synthetic hydrocarbons, the alicyclic hydrocarbons.

11. The antiperspirant cosmetic agent according to claim 1, wherein the antiperspirant aluminum salt comprises 1 to 40% by weight of the antiperspirant cosmetic agent.

12. The antiperspirant cosmetic agent according to claim 1, wherein antiperspirant aluminum salt is selected from the group of water-soluble astringent inorganic salts of aluminum, water-soluble astringent organic salts of aluminum, water-soluble astringent inorganic aluminum-zirconium salts, water-soluble astringent organic aluminum-zirconium salts, and mixtures thereof.

13. The antiperspirant cosmetic agent according to claim 1, wherein the antiperspirant is selected from the group consisting of aluminum chlorohydrate, aluminum sesquichlorohydrate, aluminum dichlorohydrate, aluminum hydroxide, potassium aluminum sulfate, aluminum bromohydrate, aluminum chloride, aluminum sulfate, aluminum chlorohydrex propylene glycol, aluminum chlorohydrex polyethylene glycol, aluminum-propylene glycol complexes, aluminum sesquichlorohydrex propylene glycol, aluminum sesquichlorohydrex polyethylene glycol, aluminum dichlorohydrex propylene glycol, aluminum dichlorohydrex polyethylene glycol, aluminum undecylenoyl collagen amino acid, sodium aluminum lactate, sodium aluminum chlorohydroxy lactate, aluminum lipoamino acids, aluminum lactate, aluminum chlorohydroxy allantoinate, sodium aluminum chlorohydroxy lactate, aluminum zirconium trichlorohydrate, aluminum zirconium tetrachlorohydrate, aluminum zirconium pentachlorohydrate, aluminum zirconium octachlorohydrate, aluminum-zirconium/propylene glycol complexes, aluminum zirconium trichlorohydrex glycine, aluminum zirconium tetrachlorohydrex glycine, aluminum zirconium pentachlorohydrex glycine, aluminum zirconium octachlorohydrex glycine, and mixtures thereof.

14. The antiperspirant cosmetic agent according to claim 1, wherein the compound of formula (PP-I) is present in a total amount of 0.05 to 20 wt. % of the antiperspirant cosmetic agent.

15. The antiperspirant cosmetic agent according to claim 1, wherein the antiperspirant cosmetic agent comprises at least one compound of formula (PP-Ia)

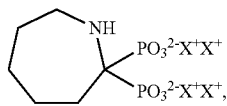

(PP-Ia)

where $X^+$ denotes $H^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt.

16. The antiperspirant cosmetic agent according to claim 1, wherein the cosmetic antiperspirant agent includes free water in a total quantity of 15 to 96% by weight based on the total weight of the antiperspirant cosmetic agent.

17. The antiperspirant cosmetic agent according to claim 1, wherein the antiperspirant cosmetic agent includes ethanol in a total quantity of 1 to 50% by weight based on the total weight of the cosmetic antiperspirant agent.

18. A method for enhancing the blocking of the sweat gland(s) and/or blocking the sweat gland(s), comprising:
applying to the skin surface of a subject at least one compound of formula (PP-I)

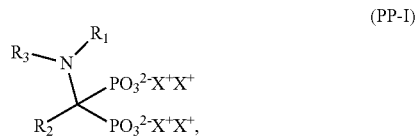

(PP-I)

where $R^1$ denotes hydrogen or a linear or branched alkyl group having 1 to 6 carbon atoms, $R^2$ and $R^3$, each independently of one another, denote a linear or branched alkyl group having 1 to 6 carbon atoms, or $R^2$ and $R^3$ form a cyclic group having 4 to 8 carbon atoms and optionally one heteroatom, selected from the group consisting of N, O, and S, and $X^+$ denotes $H^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt, wherein the weight ratio of the antiperspirant aluminum salt to the compound of formula (PP-I) is 8:1 to 1:1.

* * * * *